United States Patent

Krapcho

[11] 4,078,062
[45] Mar. 7, 1978

[54] SUBSTITUTED 2H-1,4-BENZOTHIAZIN-3(4H)-ONES

[75] Inventor: John Krapcho, Somerset, N.J.

[73] Assignee: E. R. Squibb & Sons, Inc., Princeton, N.J.

[21] Appl. No.: 736,620

[22] Filed: Oct. 28, 1976

[51] Int. Cl.$^2$ .................. C07D 279/16; C07D 417/06; C07D 279/28; A61K 31/54
[52] U.S. Cl. .................................. 424/246; 542/444; 542/442; 542/443
[58] Field of Search .................... 260/243 R; 424/246; 542/442, 443, 444

[56] References Cited

U.S. PATENT DOCUMENTS

| 2,956,054 | 10/1960 | Laubach | 260/243 |
| 3,715,353 | 2/1973 | Krapcho | 260/243 |
| 3,746,706 | 7/1973 | Krapcho | 260/243 |

*Primary Examiner*—John M. Ford
*Attorney, Agent, or Firm*—Lawrence S. Levinson; Merle J. Smith; Stephen B. Davis

[57] ABSTRACT

Compounds of the following formula and their pharmaceutically acceptable salts

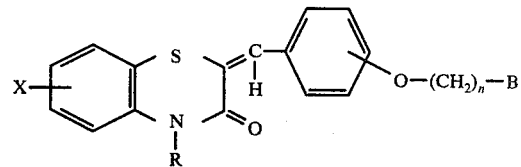

wherein X and $X_1$ are independently selected from hydrogen, halogen, lower alkyl, lower alkoxy, trifluoromethyl, nitro, or amino; R is hydrogen, lower alkyl, or

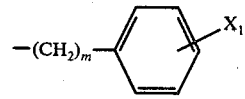

wherein *m* is 1, 2, or 3; *n* is 2, 3, 4, or 5; and B is di(lower alkyl)amino, piperidinyl, pyrrolidinyl, morpholino; or N-lower alkyl-piperazino; are disclosed. These compounds possess antiinflammatory activity.

13 Claims, No Drawings

SUBSTITUTED 2H-1,4-BENZOTHIAZIN-3(4H)-ONES

SUMMARY OF THE INVENTION

This invention relates to new compounds and their pharmaceutically acceptable salts of the formula

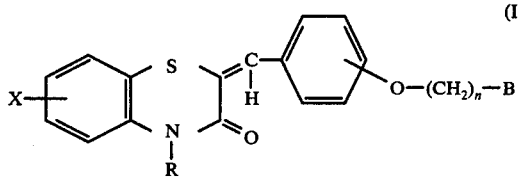

R represents hydrogen, lower alkyl, or

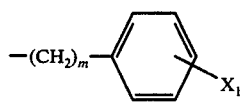

wherein
m is 1, 2 or 3.
X and $X_1$ are independently selected from hydrogen, halogen, lower alkyl, lower alkoxy, trifluoromethyl, amino, and nitro.
B represents di(lower alkyl)amino wherein each alkyl may be the same or different, piperidinyl, pyrrolidinyl, morpholinyl, or N-(lower alkyl)-piperazino.
n represents 2, 3, 4 or 5.

Preferred are the compounds of formula I and their pharmaceutically acceptable salts wherein R is hydrogen, methyl, ethyl, or

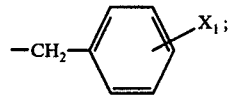

X and $X_1$ are independently selected from hydrogen, Cl, Br, methyl, methoxy, trifluoromethyl, nitro and amino; n is 2 or 3; and B is dimethylamino or diethylamino.

Most preferred are the compounds of the formula

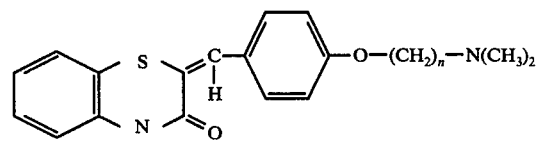

and their pharmaceutically acceptable salts wherein R is hydrogen or methyl and n is 2 or 3.

DETAILED DESCRIPTION

The terms employed above have the following meanings and such meanings are retained throughout this specification.

The term "lower alkyl" includes a straight chain hydrocarbon of from 1 to 4 carbons or a branched chain hydrocarbon of 3 carbons, i.e. methyl, ethyl, n-propyl, i-propyl, and n-butyl.

The term "lower alkoxy" includes such "lower alkyl" radicals attached to an oxygen, i.e. —O-lower alkyl.

The term "halogen" includes chlorine, bromine, and fluorine with chlorine and bromine being preferred.

The term "pharmaceutically acceptable salts" includes the pharmaceutically acceptable acid-addition salts. Acids useful for preparing these salts include hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, oxalic, and methanesulfonic acid.

The compounds of formula I and their pharmaceutically acceptable salts are prepared by reacting a 1,4-benzothiazin-3(4H)-one of the formula

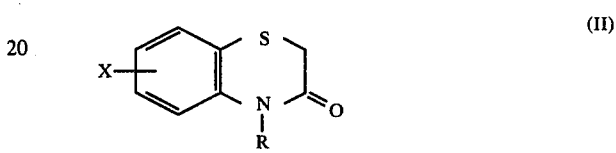

with a substituted benzaldehyde of the formula

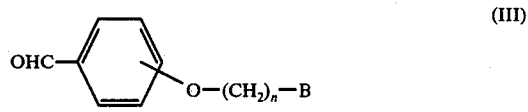

in an inert solvent such as dimethylformamide by heating at reflux temperature for several hours preferably in the presence of a base such as sodium methoxide.

The starting 1,4-benzothiazin-3(4H)-ones of formula II are prepared according to known methods as note for example U.S. Pat. No. 3,715, 353 of Krapcho. As taught in this patent an o-aminothiophenol of formula

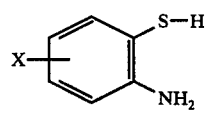

is heated with a haloacetic acid such as chloroacetic acid in the presence of about one equivalent of a base such as sodium hydroxide to yield the compound of formula II wherein R is hydrogen. This compound is then treated with a condensing agent such as sodium hydroxide, sodium amide, potassium t-butoxide, etc., in an inert solvent such as dimethylformamide followed by treatment with a sulfate or halide of the formula $(R)_2$—$SO_4$ or R—halo wherein R is lower alkyl or

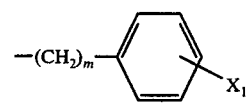

and m and $X_1$ are as defined above to yield the 4-substituted-1,4-benzothiazin-3(4H)-ones of formula II.

Similarly, the benzaldehydes of formula III are prepared by known methods as note for example U.S. Pat. No. 3,969,527 to Krapcho et al. As taught in this patent a hydroxy substituted benzaldehyde of formula

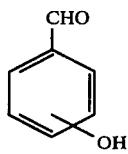

is treated with an alkaline reagent such as sodium hydride to give the corresponding sodium salt which is treated with a halo compound of formula halo—(CH$_2$)$_n$—B     (VI)

wherein n and B are as defined above.

In preparing the compounds of formula I wherein either X or X$_1$ or both are amino, it is preferred to react the 1,4-benzothiazin-3(4H)-one of formula II wherein X or X$_1$ or both are nitro with the corresponding benzaldehyde of formula III and then chemical reduce the resulting nitro product as the last step in the synthesis. The preferred reducing agent for this purpose is stannous chloride.

The compounds of formula I including their pharmaceutically acceptable salts are useful in treating inflammation in various mammalian species, e.g. rats, dogs, cats, monkeys, etc. Joint tenderness and stiffness (in conditions such as rheumatoid arthritis) are relieved by the above described compounds.

The compound or mixture of compounds of formula I including their pharmaceutically acceptable salts can be used as antiinflammatory agents according to accepted pharmaceutical practice in oral dosage forms such as tablets, capsules, elixirs, or powders, or in an injectable form in a sterile aqueous vehicle prepared according to conventional pharmaceutical practice. The compounds of this invention may be administered in amounts ranging from about 1 mg./kg./day to about 70 mg./kg./day, preferably from about 1 mg./kg./day to about 35 mg./kg./day. A preferred unit dose for use in treating a 70 kg. mammal would contain from about 70 mg. to about 1000 mg. of active ingredient.

The following examples are illustrative of the invention and represent preferred embodiments. Other modifications may be readily produced by suitable variations of the reactants. All temperatures are in the centrigrade scale.

EXAMPLE 1

2-[[4-[3-(Dimethylamino)propoxy]phenyl]methylene]-4-methyl-2H-1,4-benzothiazin-3(4H)-one, hydrochloride (1:1)

a.

2-[[4-[3-(Dimethylamino)propoxy]phenyl]methylene]-4-methyl-2H-1,4-benzothiazin-3(4H)-one, oxalate A stirred solution of 10 g. (0.056 mole) of 4-methyl-1,4-benzothiazin-3(4H)-one and 18 g. (0.093 mole) of 4-(3-dimethylaminopropoxy)benzaldehyde in 50 ml. of dimethylformamide is treated with 3.8 g. (0.07 mole) of sodium methoxide. The mixture is heated at reflux temperature for 3 hours, cooled to room temperature, and poured into 300 ml. of cold water. The resulting oily product is twice extracted with 100 ml. of ether. The ether solutions are combined, extracted with an equal volume of water, dried (MgSO$_4$), and concentrated to yield 15.3 g. of an oily residue.

This oily residue is dissolved in 75 ml. of ether and filtered to remove a small amount of insoluble material. 3.75 g. of oxalic acid dissolved in 50 ml. of ether is added and gives 17.5 g. of a yellow solid; m.p. 124°–126°, s. 100°. A solution of this material in 120 ml. of ethanol is concentrated to approximately 75 ml. and cooled overnight to give 9.8 g. of yellow solid; m.p. 160°–163°. Recrystallization from a solution containing 50 ml. of methanol and 10 ml. of dimethylformamide yields 7.8 g. of light yellow solid 2-[[4-[3-(dimethylamino)propoxy]phenyl]methylene]-4-methyl-2H-1,4-benzothiazin-3(4H)-one, oxalate; m.p. 166°–168°.

b.

2-[[4-[3-(Dimethylamino)propoxy]phenyl]methylene]4-methyl-2H-1,4-benzothiazin-3(4H)-one, hydrochloride (1:1)

The above oxalate salt is suspended in water and treated with an excess of potassium carbonate. The resulting base is extracted with ether, dried (MgSO$_4$), and concentrated to 6 g. of a yellow oily residue. A solution of this material in 50 ml. of ether is treated with one equivalent of HCl in ethanol to form 6.5 g. of crude product; m.p. 194°–196°. Recrystallization from 40 ml. of ethanol yields 5.7 g. of yellow crystals of 2-[[4-[3-(dimethylamino)propoxy]phenyl]methylene]-4-methyl2H-1,4-benzothiazin-3(4H)-one, hydrochloride (1:1), m.p. 194°–196°.

EXAMPLE 2

2-[[4-[2-(Dimethylamino)ethoxy]phenyl]methylene]-4-methyl-2H-1,4-benzothiazin-3(4H)-one, hydrochloride (1:1)

A stirred solution of 31.2 g. (0.17 mole) of 4-methyl-1,4-benzothiazin-3(4H)-one and 36.9 g. (0.19 mole) of 4-(2-dimethylaminoethyl)benzaldehyde in 125 ml. of dimethylformamide is treated with 11.8 g. (0.22 mole) of sodium methoxide. This mixture is heated at reflux temperature for 3 hours, cooled to room temperature, and poured into 500 ml. of cold water. The resulting oil is extracted twice with 200 ml. of ether. The ether solutions are combined and extracted with an equal volume of water, dried (MgSO$_4$), and concentrated to approximately half its volume during which time crystallization occurred. After cooling overnight, the product is filtered and washed with a small amount of cold hexane to yield 16.5 g. of yellow crystals; m.p. 81°–83°. Recrystallization from 40 ml. of cyclohexane yields 15 g. of yellow 2-[[4-[2-(dimethylamino)ethoxy]phenyl]methylene]-4-methyl-2H-1,4-benxothiazin-3(4H)-one; m.p. 82°–84°.

A solution of 4.5 g. of 2-[[4-[2-(dimethylamino)ethoxy]phenyl]methylene]-4-methyl-2H-1,4-benzothiazin-3(4H)-one in 15 ml. of warm acetonitrile is cooled to 25° and treated with one equivalent of hydrochloric acid in ethanol to yield 4.8 g. of yellow crystals; m.p. 199°–201°. Recrystallization from 35 ml. of ethanol yields 4.2 g. of yellow 2-[[4-[2-(dimethylamino)ethoxy]phenyl]methylene]-4-methyl-2H-1,4-benzothiazin-3(4H)-one, hydrochloride (1:1); m.p. 199 –201°.

EXAMPLE 3

2-[[4-[3-(Dimethylamino)propoxy]phenyl]methylene]-2H-1,4-benzothiazin-3(4H)-one, hydrochloride (1:1)

A solution of 25 g. (0.15 mole) of 1,4 -benzothiazin-3(4H)-one in 125 ml. of dimethylformamide is reacted with 52 g. (0.25 mole) of 4-(3-dimethylaminopropoxy)-benzaldehyde and 10.2 g. of sodium methoxide according to the procedure of example 1 to yield 34.4 g. of crude yellow product; m.p. 144°–147°, s. 140°. Recrystallization from 75 ml. of ethanol yields 24.2 g. of yellow crystalline 2-[[4-[3-(dimethylamino)propoxy]phenyl]methylene]-2H-1,4-benzothiazin-3(4H)-one; m.p. 156°–158°.

A solution of 6 g. of the above product in 30 ml. of chloroform is treated with one equivalent of hydrochloric acid in ethanol to yield 5.6 g. of yellow solid; m.p. 224°–226°. A solution of this material in 110 ml. of hot methanol is concentrated to approximately half its volume, and then cooled overnight to yield 4.2 g. of yellow crystalline 2-[[4-[3-(dimethylamino)propoxy]phenyl]methylene]-2H-1,4-benzothiazin-3(4H)-one; hydrochloride (1:1); m.p. 224°–226°.

EXAMPLE 4

2-[[4-[2-(Dimethylamino)ethoxy]phenyl]methylene]-2H-1,4-benzothiazin-3(4H)-one, hydrochloride (1:1)

A solution of 25 g. (0.15 mole) of 1,4-benzothiazin-3(4H)-one in 125 ml. of dimethylformamide is reacted with 48.5 g. (0.25 mole) of 4-(2-dimethylaminoethoxy)-benzaldehyde and 10.2 g. (0.18 mole) of sodium methoxide according to the procedure of example 1 to yield 36.8 g. of crude yellow product; m.p. 134°–137°. Crystallization from 100 ml. of ethanol yields 28.1 g. of material; m.p. 158°–160°, s. 145°. Recrystallization from 50 ml. of dimethylformamide yields 22.8 g. of yellow crystalline (2-[[4-[2-(dimethylamino)ethoxy]phenyl]methylene]2H-1,4-benzothiazin-3(4H)-one; m.p. 177°–179°.

A solution of 5 g. of the above product in 50 ml. of chloroform is treated with one equivalent of hydrochloric acid in ethanol to yield 4.8 g. of yellow product; m.p. 222°–224°. Recrystallization from 30 ml. of methanol yields 4.6 g. of yellow crytalline 2-[[4-[2 -(dimethylamino)ethoxy]phenyl]methylene]-2H-1,4-benzothiazin-3(4H)-one, hydrochloride (1:1); m.p. 224°–226°.

EXAMPLES 5–30

Following the procedure of examples 1 to 4 but employing the substituted 1,4-benzothiazin-3(4H)-one of Col. I and the substituted benzaldehyde of Col. II one obtains the final product shown in Col. III.

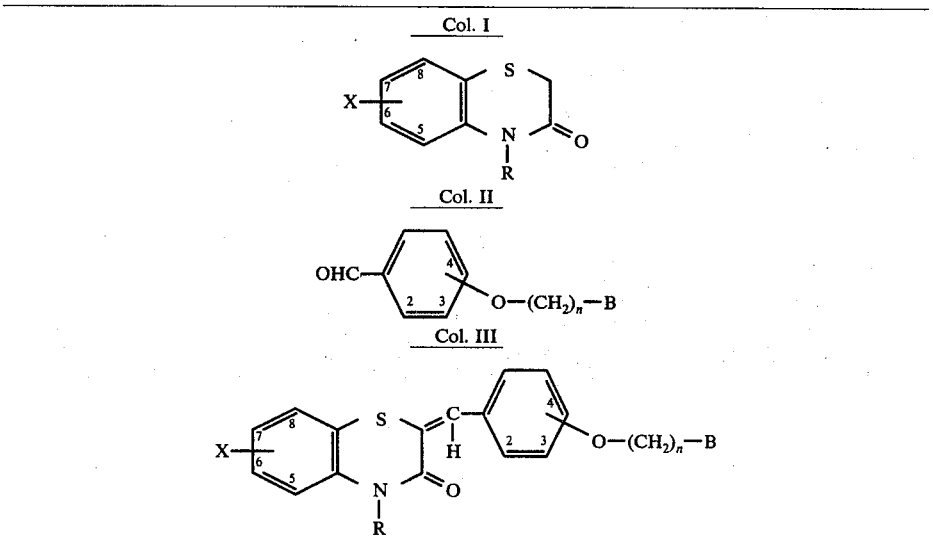

| Ex. | X | R | —O—(CH$_2$)$_n$—B |
|---|---|---|---|
| 5 | H | —CH$_3$ | —O—(CH$_2$)$_4$—N(CH$_3$)$_2$ (4-position) |
| 6 | Cl (5-position) | —H | —O—(CH$_2$)$_5$—N(CH$_3$)$_2$ (4-position) |
| 7 | Br (6-position) | —C$_2$H$_5$ | —O—(CH$_2$)$_3$—N(C$_2$H$_5$)$_2$ (4-position) |
| 8 | F (8-position) | —n-C$_3$H$_7$ | —O—(CH$_2$)$_2$—N(C$_2$H$_5$)(CH$_3$) (3-position) |
| 9 | CH$_3$ (7-position) | —i-C$_3$H$_7$ | —O—(CH$_2$)$_3$—N(CH$_3$)$_2$ (2-position) |
| 10 | OC$_2$H$_5$ (6-position) | —H | —O—(CH$_2$)$_3$—N(n-C$_3$H$_7$)$_2$ (4-position) |
| 11 | CF$_3$ (5-position) | —CH$_3$ | —O—(CH$_2$)$_4$—N(n-C$_3$H$_7$)(CH$_3$) (4-position) |
| 12 | NH$_2$ (7-position) | —CH$_2$—C$_6$H$_5$ | —O—(CH$_2$)$_2$—N(n-C$_4$H$_9$)$_2$ (4-position) |
| 13 | NO$_2$ (8-position) | —(CH$_2$)$_2$—C$_6$H$_5$ | —O—(CH$_2$)$_5$—N(CH$_3$)$_2$ (3-position) |
| 14 | H | —(CH$_2$)$_3$—C$_6$H$_5$ | —O—(CH$_2$)$_2$—N(CH$_3$)$_2$ (2-position) |

-continued

Col. I

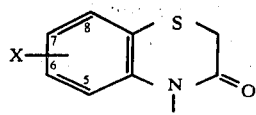

Col. II

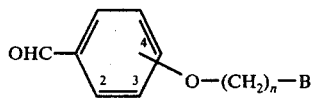

Col. III

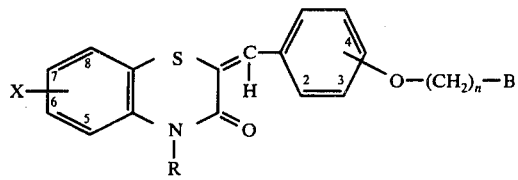

| Ex. | X | R | $-O-(CH_2)_n-B$ |
|-----|---|---|---|
| 15 | Cl (7-position) | $-CH_2-\phantom{x}\bigcirc\phantom{x}-OCH_3$ | $-O-(CH_2)_3-N(C_2H_5)(CH_3)$ (4-position) |
| 16 | OCH$_3$ (5-position) | $-(CH_2)_2-\phantom{x}\bigcirc\phantom{x}-Cl$ (3-Cl) | $-O-(CH_2)_4-N(CH_3)_2$ (4-position) |
| 17 | H | $-n$-C$_4$H$_9$ | $-O-(CH_2)_3-N(i$-C$_3$H$_7)_2$ (4-position) |
| 18 | C$_2$H$_5$ (7-position) | $-CH_2-\phantom{x}\bigcirc\phantom{x}-CH_3$ | $-O-(CH_2)_3-N(CH_3)_2$ (2-position) |
| 19 | H | $-$H | $-O-(CH_2)_3-N\langle\text{piperidine}\rangle$ (4-position) |
| 20 | H | $-$CH$_3$ | $-O-(CH_2)_2-N\langle\text{piperidine}\rangle$ (4-position) |
| 21 | Cl (6-position) | $-CH_2-\phantom{x}\bigcirc$ | $-O-(CH_2)_4-N\langle\text{piperidine}\rangle$ (3-position) |
| 22 | CH$_3$ (7-position) | $-$C$_2$H$_5$ | $-O-(CH_2)_3-N\langle\text{piperidine}\rangle$ (2-position) |
| 23 | OCH$_3$ (6-position) | $-(CH_2)_2-\phantom{x}\bigcirc\phantom{x}-Cl$ | $-O-(CH_2)_3-N\langle\text{morpholine}\rangle$ (4-psoition) |
| 24 | H | $-$H | $-O-(CH_2)_2-N\langle\text{morpholine}\rangle$ (3-position) |
| 25 | H | $-$CH$_3$ | $-O-(CH_2)_5-N\langle\text{piperidine}\rangle$ (4-position) |
| 26 | H | $-i$-C$_3$H$_7$ | $-O-(CH_2)_3-N\langle\text{piperazine}\rangle-$CH$_3$ (4-position) |

-continued

Col. I

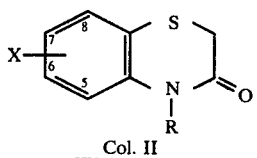

Col. II

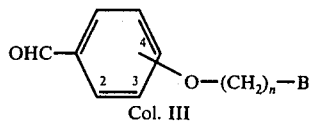

Col. III

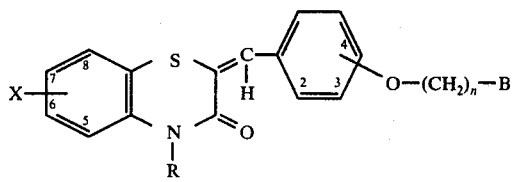

| Ex. | X | R | —O—(CH$_2$)$_n$—B |
|---|---|---|---|
| 27 | NH$_2$ (8-position) | —H | —O—(CH$_2$)$_4$—N⌒N—C$_2$H$_5$ (3-psoition) |
| 28 | Cl (8-position) | —(CH$_2$)$_3$—⟨phenyl⟩ | —O—(CH$_2$)$_5$—N⌒N—CH$_3$ (4-position) |
| 29 | H | —CH$_2$—⟨phenyl⟩ | —O—(CH$_2$)$_2$—N⌒N—n-C$_3$H$_7$ (2-position) |
| 30 | H | —CH$_3$ | —O—(CH$_2$)$_3$—N⌒N—CH$_3$ (4-position) |

What is claimed is:

1. A compound of the formula

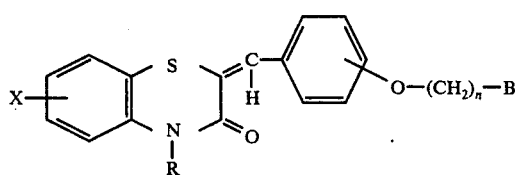

wherein R is hydrogen, lower alkyl, or

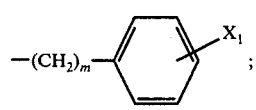

X and X$_1$ are independently selected from the group consisting of hydrogen, halogen, lower alkyl, lower alkoxy, trifluoromethyl, nitro and amino; $m$ is 1, 2 or 3; $n$ is 2, 3, 4, or 5; and B is di(lower alkyl)amino wherein each lower alkyl is the same or different, piperidinyl, pyrrolidinyl, morpholino, or N-lower alkyl-piperazino; and a pharmaceutically acceptable salt thereof.

2. The compound of claim 1 wherein R is hydrogen, methyl, ethyl, or

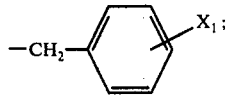

X and X$_1$ are independently selected from the group consisting of hydrogen, methyl, methoxy, Cl, Br, trifluoromethyl, amino, and nitro; $n$ is 2 or 3; B is dimethylamino or diethylamino; and a pharmaceutically acceptable salt thereof.

3. The compound of claim 2 of the formula

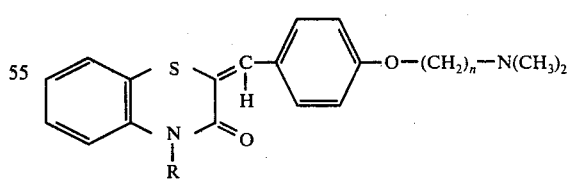

wherein R is hydrogen or methyl; $n$ is 2 or 3; and a pharmaceutically acceptable salt thereof.

4. The compound of claim 3, 2-[[4-[3-(dimethylamino)propoxy]phenyl]methylene]-4-methyl-2H-1,4-benzothiazin-3(4H)-one.

5. The hydrochloride salt of the compound of claim 4.

6. The compound of claim 3, 2-[[4-[2-(dimethylamino)ethoxy]phenyl]methylene]-4-methyl-2H-1,4-benzothiazin-3(4H)-one.

7. The hydrochloride salt of the compound of claim 6.

8. The compound of claim 3, 2-[[4-[3-(dimethylamino)-propoxy]phenyl]methylene]-2H-1,4-benzothiazin-384H)-one.

9. The hydrochloride salt of the compound of claim 8.

10. The compound of 3, 2-[[4-[2-(dimethylamino)ethoxy]phenyl]methylene]-2H-1,4-benzothiazin-3(4H)-one.

11. The hydrochloride salt of the compound of claim 10.

12. A pharmaceutical composition useful for treating inflammation in a mammalian specie comprising from about 1 mg./kg. to about 70 mg./kg. of a compound or mixture of compounds of claim 1 and a pharmaceutically acceptable carrier.

13. The method of treating inflammation in a mammalian specie comprising administering an effective amount of the composition of claim 12.

* * * * *

UNITED STATES PATENT OFFICE
CERTIFICATE OF CORRECTION

Patent No. 4,078,062     Dated March 7, 1978

Inventor(s) John Krapcho

It is certified that error appears in the above-identified patent and that said Letters Patent are hereby corrected as shown below:

Column 11, line 11, "thiazin-384H)-one." should read
--- thiazin-3 (4H) -one. ---.

Signed and Sealed this

Tenth Day of October 1978

[SEAL]

Attest:

RUTH C. MASON
*Attesting Officer*

DONALD W. BANNER
*Commissioner of Patents and Trademarks*